(12) United States Patent
Takahashi et al.

(10) Patent No.: US 9,012,205 B2
(45) Date of Patent: Apr. 21, 2015

(54) REVOLVING CELL CULTURE CARTRIDGE AND METHODS OF USE

(75) Inventors: Shuichiro Takahashi, Tokyo (JP); Hiroyuki Takahashi, Tokyo (JP)

(73) Assignee: Empire Technology Development LLC, Wilmington, DE (US)

( * ) Notice: Subject to any disclaimer, the term of this patent is extended or adjusted under 35 U.S.C. 154(b) by 300 days.

(21) Appl. No.: 13/264,977

(22) PCT Filed: Apr. 18, 2011

(86) PCT No.: PCT/US2011/032922
§ 371 (c)(1),
(2), (4) Date: Oct. 17, 2011

(87) PCT Pub. No.: WO2012/144983
PCT Pub. Date: Oct. 26, 2012

(65) Prior Publication Data
US 2012/0264160 A1    Oct. 18, 2012

(51) Int. Cl.
*C12M 1/34*    (2006.01)
*C12M 3/00*    (2006.01)
*C12M 1/32*    (2006.01)
(Continued)

(52) U.S. Cl.
CPC ............... *C12M 23/12* (2013.01); *C12M 23/44* (2013.01); *C12M 25/04* (2013.01); *C12M 23/50* (2013.01); *G01N 33/5005* (2013.01)

(58) Field of Classification Search
CPC .................. G01N 33/54366; G01N 33/54373; G01N 33/5008; G01N 33/5011; G01N 35/025; G01N 2035/00366; B01J 2219/00722; B01J 19/0046; B82Y 30/00; C12Q 1/04; C12Q 1/02; C12Q 1/18; B01L 3/50851; B01L 9/52; B01L 3/50853; B01L 7/52; B01L 2200/0689; B01L 2300/0803; B01L 2300/1805; B01L 2300/1861; B01L 2300/041
USPC .................................................. 435/29, 287.1
See application file for complete search history.

(56) References Cited

U.S. PATENT DOCUMENTS 5,219,526 A  *  6/1993  Long ................................ 422/64
6,103,479 A       8/2000  Taylor
(Continued)

FOREIGN PATENT DOCUMENTS

EP         1953552 B1      4/2010
WO    2004/095034 A1     11/2004
(Continued)

OTHER PUBLICATIONS

International Search Report dated Aug. 23, 2011 as received in related application No. PCT/US2011/032922.
Rose Scientific Ltd., Multi-floor Flasks, Tissue Culture Products, pp. 2, Alberta, Canada, Sep. 1, 2011.
BD Biosciences, BD Falcon Cell Culture Inserts, www.bdbiosciences.ca, Apr. 12, 2010, Becton, Dickenson and Company, Franklin Lakes, New Jersey.

*Primary Examiner* — Michael Hobbs
(74) *Attorney, Agent, or Firm* — Maschoff Brennan

(57) ABSTRACT

A cell culture device and system can be used for high throughput biological assays to study the biological effect of a test substance. The device and system can include a revolving cartridge having a body including a center aperture and two or more evenly spaced sample wells that are spaced apart from each adjacent sample well by at least the diameter of each sample well. Each sample well can be positioned radially equidistant from the center aperture. Each sample well can have a fluid permeable membrane base configured to fluidly couple a top surface and a bottom surface of the body.

20 Claims, 9 Drawing Sheets

(51) Int. Cl.
*C12M 1/12* (2006.01)
*C12M 1/00* (2006.01)
*G01N 33/50* (2006.01)

(56) References Cited

U.S. PATENT DOCUMENTS

2002/0047003 A1 4/2002 Bedingham et al.
2003/0054542 A1 3/2003 Burns et al.
2006/0019410 A1 1/2006 St. Claire
2008/0286839 A1 11/2008 Hsu
2009/0034358 A1 2/2009 Brod et al.

FOREIGN PATENT DOCUMENTS

| WO | 2006/117541 A1 | 11/2006 |
| WO | 2007/022026 A2 | 2/2007 |
| WO | 2009/103416 A1 | 8/2009 |
| WO | 2010/042072 A1 | 4/2010 |

* cited by examiner

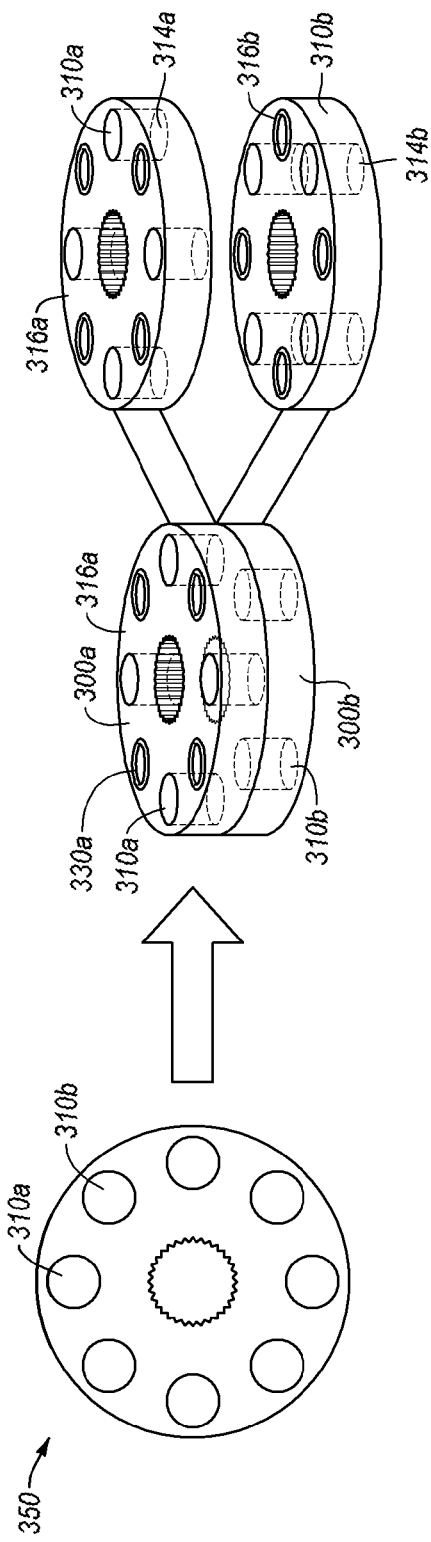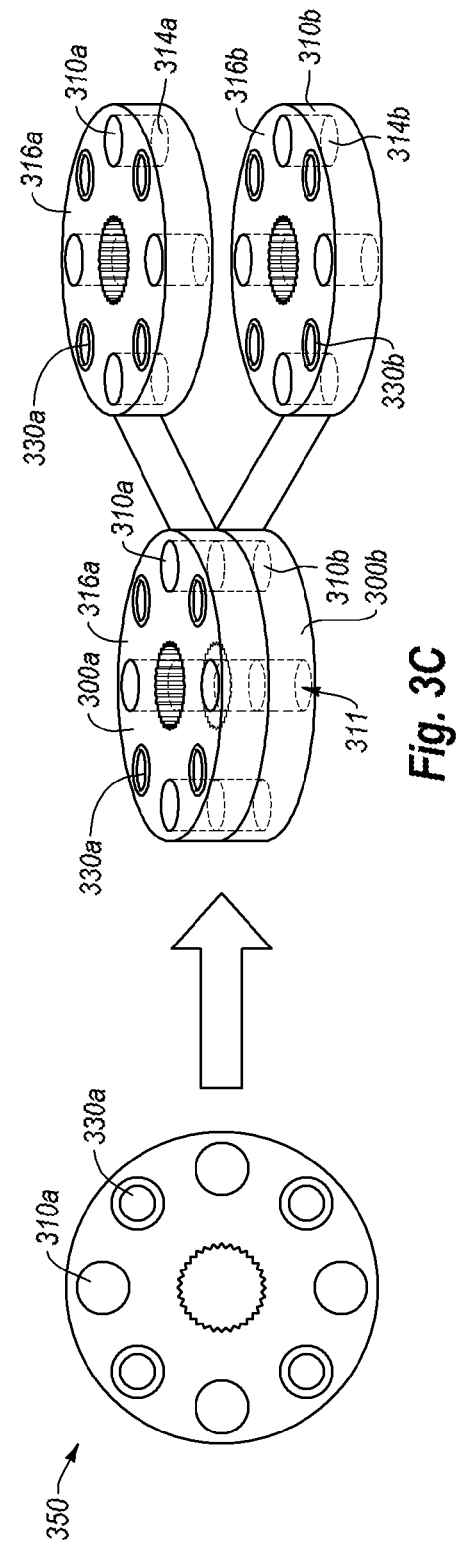

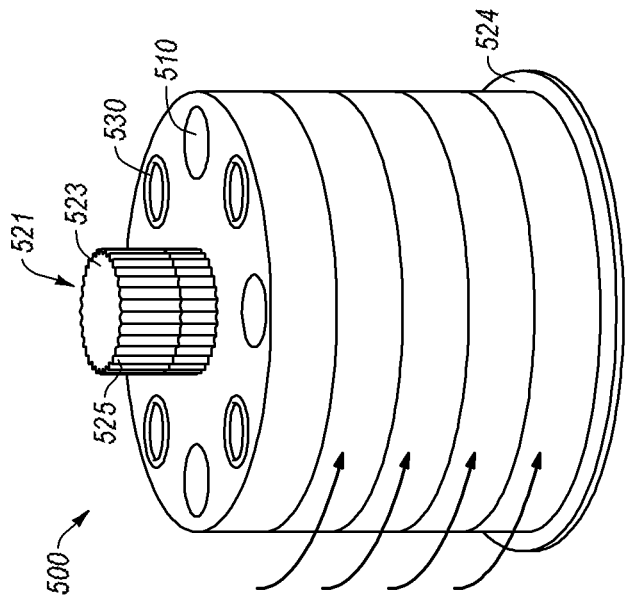
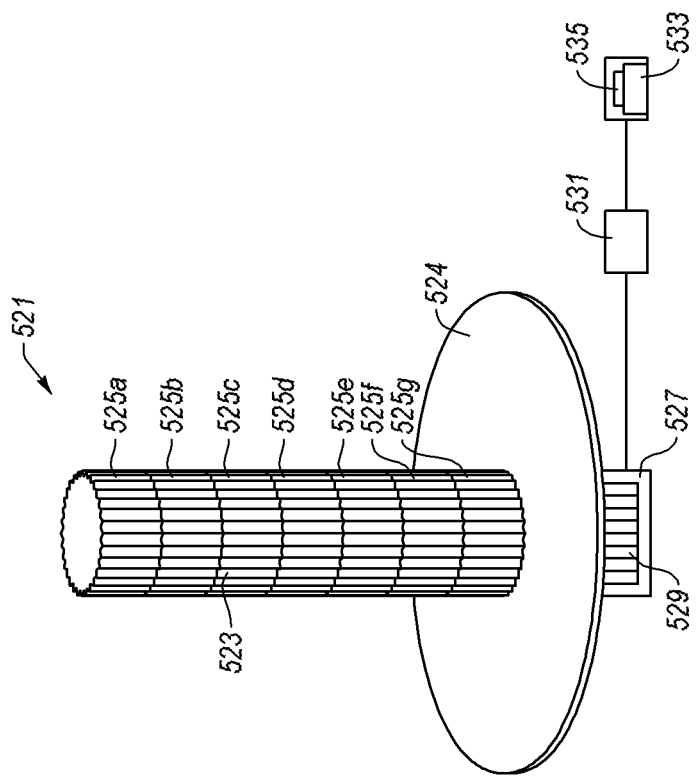
Fig. 5A
Fig. 5B

REVOLVING CELL CULTURE CARTRIDGE AND METHODS OF USE

The present application is a U.S. National Stage of International Application No. PCT/US2011/032922, filed on Apr. 18, 2011.

BACKGROUND

Various types of devices have been designed for studying the effects of substances on biological components. Usually, the devices are multi-well plates that are used to test one or more substances only on the cells of a single well. In order for a biological pathway to be tested in response to a substance, the contents of a well previously exposed to the substance may have to be manually withdrawn and placed into a new well. As such, the current technology does not provide a suitable device or method for studying the cascading effects of a substance on biological components in a biological pathway.

With regard to toxicity tests, a significant amount of time and money may be expended in order to carry out environmental toxicity tests on chemical substances or toxicity tests on new drug candidate substances. A number of lengthy toxicity testing procedures on a variety of cell species and organism species are conducted. Various biological components (e.g., proteins, cells, and microorganisms) are likely to be involved in the practical mechanisms of environmental toxicity or toxic damage and detoxification metabolism of living organisms. However, current "one substance on one cell type" tests that examine toxic effects of a substance on specific cells are not sufficient or conducive to assaying or understanding the complex biological cascade of events involving a significant amount of biological components.

In view of the foregoing, it would be beneficial to have an improved biological assay device and system that is sufficient to perform comprehensive assessments of the biological activity of substances.

SUMMARY

In one embodiment, a cell culture device and system can be used for high throughput biological assays to study the biological effect of a test substance. The device and system can include a revolving cartridge having a body including a center aperture and two or more evenly spaced sample wells that are spaced apart from each adjacent sample well by at least the diameter of each sample well. Each sample well can be positioned radially equidistant from the center aperture. Each sample well can have a fluid permeable membrane base configured to fluidly couple a top surface and a bottom surface of the body. The cell culture system can include two or more of the revolving cartridges in a stacked or un-stacked arrangement. When stacked, the revolving cartridges can be located on a spindle, which may be operably coupled to a mechanical system that can rotate the revolving cartridges independently. The mechanical system can be operably coupled to a controller and/or computing system, and can be controlled in response to computer-executable instructions stored on a storage device of the computing system.

Biological assays can be conducted with two or more revolving cartridges. The biological assay can be conducted as follows: introducing one or more biological substances into one or more sample wells of the one or more revolving cartridges; introducing one or more test substances and/or one or more control substances to the one or more biological substances; and assaying the biological substances to determine a biological activity of the one or more test substances on the one or more biological substances.

In one embodiment, the biological assay can include: (a) allowing or inducing apoptosis or inflammation reactions to occur in one or more test compositions in one or more sample wells of a higher revolving cartridge; (b) eluting one or more test compositions from the higher revolving cartridge to one or more sample wells of a lower revolving cartridge; and optionally, repeating steps (a) and (b) into one or more lower revolving cartridges.

In one embodiment, the biological assay can include: incubating one or more test components in one or more sample wells of a first revolving cartridge with one or more epithelial cells so as to produce one or more first test compositions; eluting the one or more first test compositions of the one or more sample wells in the first revolving to one or more sample wells in a second revolving; incubating the one or more first test compositions with immune system biological substances and/or cells in one or more sample wells of the second revolving; and determining whether or not the one or more test components cause the one or more epithelial cells to produce an immune product.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIGS. 2A-2B include schematic representations of a cross-sectional profile of a sample well in a revolving cell culture cartridge that has a liquid permeable membrane.

FIGS. 3A-3C include schematic representations of an embodiment of a biological assay system having a stack of revolving cell culture cartridges in aligned and staggered orientations.

FIGS. 5A-5C include schematic representations of an embodiment of a biological assay system having a stack of revolving cell culture cartridges on an operable spindle that can be controlled mechanically and by computer-executable instructions.

DETAILED DESCRIPTION

Figure 1A:
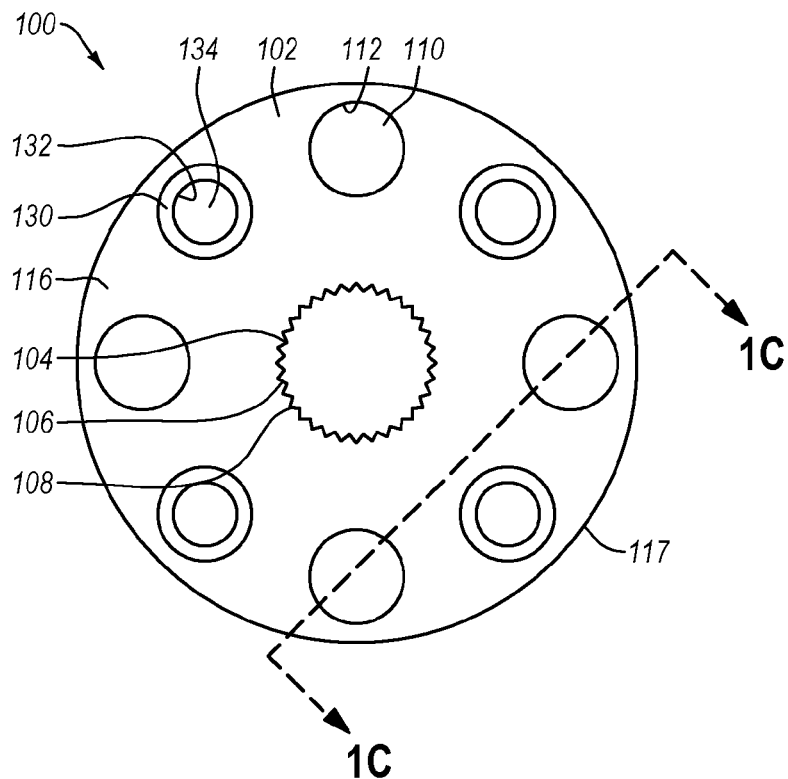
FIGS. 1A-1C include schematic representations of an embodiment of a revolving cell culture cartridge.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Generally, one or more revolving cartridges can be configured for use in biological experiments to test whether or not one or more test substance have a biological effect on a biological substance. The revolving cartridges can include one or more wells that are configured to be capable of containing a biological substance so that biological activity of a test substance can be assayed with respect to the biological substance. Some non-limiting examples of test substances, which are described in more detail below, can include one or more natural or synthetic chemicals that may or may not have a known toxicity or biological effect such as bis-phenol A (BPA), polyaromatic hydrocarbons, food additives or preservatives, heavy metals, DNA intercalators, or others. Some non-limiting examples of biological substances, which are described in more detail below, can include one or more natural or recombinant or modified organisms, organ systems, individual organs, tissues, extracellular matrices, cells, organelles, cellular components, proteins, receptors, cytokines, portions thereof, and the like.

The wells can be configured to retain the biological substance therein throughout an experiment as well as during analysis of changes to the biological substance in response to the test substance. Individual wells can each include a semi-permeable membrane as a substrate for the biological substance that does not allow for the biological substance to pass therethrough. On the other hand, the semi-permeable membrane is configured to allow the test substance to pass therethrough after interacting for a sufficient time with the biological substance. As such, the well can include a cap and/or plug to inhibit the test substance from passing through the semi-permeable membrane. Once the cap and/or plug is removed or disassociated with the well, the test substance can then pass through the semi-permeable membrane by gravity or by use of pressure. In one example, both the test substance and biological substance can be biological in nature, with the difference being that the test substance can pass through the semi-permeable membrane while the biological substance cannot pass through the semi-permeable membrane. In another example, the larger of the substances can be the biological substance while the smaller is the test substance.

The revolving cartridges can be stacked so that an upper and/or lower revolving cartridge can function as a cap and/or plug for a particular revolving cartridge. For example, the wells of the stacked revolving cartridges can be unaligned for cap and/or plug functionality. In another example, the wells of the stacked revolving cartridges can be aligned so that two more sequential wells can be aligned to form a conduit. This conduit can allow for the test substance and/or any other substance in the well (other than the biological substance) to be passed to the lower well. The other substances can be an assay medium as well as substances that are generated or altered from the interaction between the test substance and the biological substance. For example, the test substance may be metabolized by the biological substance, and the metabolite can be passed to the lower well for interaction with another biological substance that can be the same as the previous biological substance of the upper well or a different biological substance. This allows for stacked revolving cartridges to include multiple biological substances to be tested with the test substance. In one instance, the multiple biological substances can be related, naturally occurring in a common tissue and/or cell, or be included with a biological pathway as well as biological substances that are upstream or downstream of a particular biological pathway or in related or unrelated biological pathways. The selection of the multiple biological substances can be used to assess the impact of a test substance on a biological system and related and unrelated biological substances as well as the impact upstream or downstream of a particular biological substance or biological pathway. For simplicity, the multiple biological substances are described herein with relation to biological pathways; however, this is merely one example of the different types of biological substances and relationships thereof, and the disclosure herein can be applied to a wide assortment of biological substances both related and unrelated.

A stack of revolving cell culture cartridges (i.e., revolving cartridge) can be used for biological pathway analysis. The stack of revolving cartridges can be employed in a high throughput system that can study the effects of a substance on a biological pathway. The high throughput system can be used to determine the toxicity of substances as well as the potential therapeutic benefit of substances. For example, the system can be used to analyze comprehensive detoxification metabolism of a plurality of organism species or cell species in a single toxicity test. Since rotating the revolvers enables arbitrary combinations of biological reactions and cell species, it provides for efficient high throughput screening assays.

In one example, the wells can include biological substances that are useful in determining toxicity, such as unicellular organisms and cells that have differentiated into liver cells or heart muscles that can be used for toxicity tests on living organisms. Cell organelles, such as mitochondria, or even individual types of proteins can also be used.

Figure 1B:
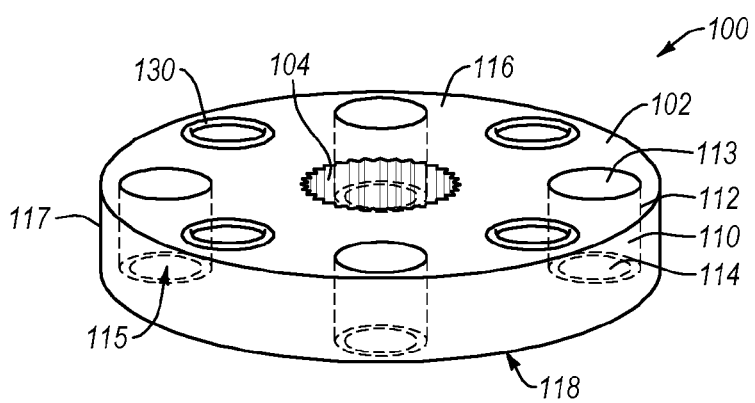
Figure 1C:
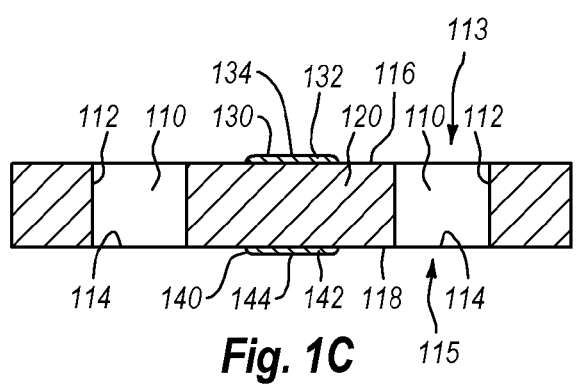

The revolving cartridges can include a vessel having a plurality of wells formed at regular intervals along a circle or series of circles that shares a center axis with a center aperture of the vessel (see FIGS. 1A-1C). While the figures illustrate the revolving cartridges as being substantially circular disks, other shapes and relative dimensions can also be used. For example, the body of the vessel as well as the individual wells can have a cross-sectional profile that is circular, oval, square, rectangle, triangle, or other shape or polygon. Also, while the figures show the vessel to be wider than tall, the vessel can indeed be taller than it is wide. Various permutations of shape and size can be used. Alternatively, the vessel can be prepared with only one well located radially from the center aperture.

The center aperture of the cylindrical vessel can be configured for receiving a center shaft that stacks multiple cylindrical vessels. The semi-permeable membrane can be configured as a filter through which test substances, secondary cell metabolites, and ions can pass through. Also, the semi-permeable membrane can be configured to discharge a medium such as a liquid or substances dissolved and/or suspended in the medium through the bottom of the well while retaining the biological substance therein. The permeability of the semi-permeable membrane can be selected or configured in view of the test substance, metabolites thereof, and/or the biological substance such that the biological substance is retained within the well while the test substance and corresponding metabolites can pass therethrough. For example, the semi-permeable membrane can function as a size-exclusion separator so that the relative size of the test substance and metabolites compared to the biological substance can be used for the size cut-off of substances that can and cannot pass through the semi-permeable membrane.

The plugs and/or caps for the wells of the revolving cartridge can have various configurations; however, gaskets or o-rings made of a flexibly resistant material can be useful to seal the wells as described in more detail below. The center aperture and caps/plugs can be useful so that a stack of revolving cartridges can be rotated relative to each other so that the wells are in an offset position with respect to vertically adjacent revolving cartridges, which can prevent the test substance or reaction medium or solution from flowing into the next lower revolving cartridge well. The revolving cartridges can also be rotated relative to each other so that the wells of two or more vertically adjacent wells can be aligned to form a conduit for the test substance or reaction medium or solution to pass through.

In one example, the revolving cartridge and center aperture can be configured so as to be receivable in a centrifuge (e.g., rack-in-rotor types of Tomy Seiko Co., Ltd.). The revolving cartridges can then be centrifuged for collecting cells after tests, or extracting nucleic acids as well as other centrifuge functions.

Cell species to be analyzed for biological response to test and control substances can be placed selectively in one or more sample wells in the one or more stacked revolving cartridges. The order of the stacked revolving cartridges and thereby the order of the biological substances, from the top to the bottom, can correspond to the reaction process order of a biological pathway. For example, a particular biological pathway, such as a metabolic pathway, can include a sequence of proteins or components that interact with a substance or resulting metabolite in sequence in order to metabolize the substance, and the stacked revolving cartridges can include these proteins or components in sequence from top to bottom. This allows for a test substance to interact with a first protein or component (i.e., first biological substance) in an upper well before the test substance or metabolite thereof passes to an adjacent, lower well having the next protein or component (e.g., second biological substance) in the biological pathway. This configurations allows for the systematic and sequential testing of how a test substance interacts with the biological substances in a particular sequence. The revolving cartridges in a stack can be rearranged so that the test substance can be studied with a different order of biological substances.

During a reaction in a revolving cartridge well, the stack is set to be offset so that the caps or plugs on the surface of the next revolving cartridge directly overtop or underneath can seal the wells of the former revolving cartridge. Once the test substance and biological substance have interacted for a suitable or particular period of time, the revolving cartridges can be rotated so that adjacent wells are aligned to form a conduit so that the test substance or metabolites thereof can pass to the lower well in order to interact with the biological substance in the lower well.

A biological assay can be conducted by determining a test substance to be studied, and then determining the biological substances, such as cells, to be studied in the presence of the test substance. The biological substances can be loaded into the sample wells of a stack of revolving cartridges, which are then located onto a spindle, with the revolving cartridges set to the planned reaction path. Alternatively, the reaction path of vertically adjacent wells can be arbitrary or random as well as known or unknown. The test substance and any control substances can be introduced into one or more sample wells of the top revolving cartridge with the wells in an offset orientation so that the top wells do not form conduits with the lower wells. After a biological reaction between the test substance and the biological substance, the revolving cartridge can be rotated so that the top wells and bottom wells form a conduit so that the contents of the top well can flow into the "next lower" bottom well for a biological interaction with the biological substances of the lower wells. This process can be repeated for each revolving cartridge. The contents of the individual wells, and particularly contents from the bottom well, can be examined for biological effect from the test substance (e.g., examined for residual toxicity to analyze the detoxification metabolism of each flow path). Each revolving cartridge can optionally be centrifuged for collecting cells, extracting nucleic acids, or for expression analysis of genes and proteins, among others.

Since all the chemical substances in an upper well including secondary metabolites (except for cells) may be introduced into a lower well, this system enables the analysis of biological pathways (e.g., detoxification paths) by unknown mechanisms that include plurality of contributing factors and involve a plurality of biological substances.

FIGS. 1A-1C illustrate an embodiment of a cell device in the form of a revolving cartridge 100 that can be used in biological assays. The revolving cartridge 100 can be formed from a body 102 that defines features of the revolving cartridge 100 having a top surface 116, a bottom surface 118, and a perimeter surface 117. The body 102 can include surfaces that define a center aperture 104 and two or more sample wells 110. The body 102 can also include surfaces that define two or more plug members 130. The body 102 can include a top surface 116 that defines a top opening 113 for each sample well 110 such that the sample well 110 is open at the top surface 116. The top surface 116 can also define the two or more plug members 130. Optionally, the bottom surface 118 can define the two or more cap members 140. The body 102 can also include a bottom surface 118 that defines a bottom opening 115 for each sample well 110 such that the sample well 110 is open at the bottom surface 116. Each sample well 100 can include a semi-permeable membrane base 114 that is positioned in the sample well 100 between the top opening 113 and the bottom opening 115. For example, the semi-permeable membrane can be a fluid permeable membrane where solids or larger substances cannot pass through while allowing small substances or solubilized or suspended substances in the fluid to pass therethrough. Molecular weights can be used to establish the permeability cut-off.

As shown, the revolving cartridge 100 can have a body 102 that defines a center aperture 104 and two or more evenly spaced sample wells 110 that are spaced apart from each adjacent sample well 110 by at least the diameter of each sample well 110. Each sample well 110 can be positioned radially equidistant from the center aperture 104 so that each sample well 100 is an equal distance from the center aperture 104. Also, each sample well 100 can be equally spaced around the center aperture 104. Each sample well 110 can have a semi-permeable membrane base 114 configured to couple (e.g., fluidly couple) the top surface 116 and a bottom surface 118 of the body 102.

The center aperture 104 is configured to receive a shaft or spindle therethrough which allows for the shaft or spindle to rotate the revolving cartridge 100. The center aperture 104 is defined by one or more walls 106 or surfaces of the body 102. The one or more walls 106 cooperatively form the shape 108 of the aperture 104 such that the aperture 104 is configured to receive a shaft 521 (see FIG. 5A) therethrough. The shape 108 of the aperture 104 can be configured similar to gears in that the aperture 104 can receive and mate with the shaft 521.

Accordingly, the aperture 104 and the shaft 521 can be designed to be operably coupled together. As such, the one or more walls 106 of the center aperture 104 can be configured to rotatably engage with the shaft 521. The one or more walls 106 and the shaft 521 can be configured to mate such that the revolving cartridge 100 is fixed with respect to the shaft 521. Thus, the one or more walls 106 and shaft 521 are configured such that rotation of the shaft 521 rotates the revolving cartridge 100 and when the shaft 521 is static the revolving cartridge 100 is static.

The body 102 can be configured such that each one of the sample wells 110 has a top opening 113 formed into the top surface 116 of the body 102, and has a bottom opening 115 formed into a bottom surface 118 of the body 102. Each sample well 110 can be defined by a sample well wall 112. Each sample well 110 has a semi-permeable membrane 114 which can be placed at various positions between the top opening 113 and the bottom opening 115. In one example, the semi-permeable membrane base 114 is positioned at or adjacent to the bottom opening 115 so as to be at or adjacent to the bottom surface 118 of the body 102. The semi-permeable membrane base 114 can be spaced from the bottom opening 115 and/or bottom surface 118 so that there is enough space to receive a plug member 130 to seal the bottom opening 115. Also, the semi-permeable membrane base 114 can be spaced from the top opening 113 and/or top surface 116 so that there is enough space to receive a cap member 140 to seal the top opening 115.

In one example, the semi-permeable membrane base 114 can be substantially parallel with one of a top surface 116 or bottom surface 118 of the body 102 (FIG. 2A). In another example, the semi-permeable membrane base 114 can be substantially perpendicular with respect to a center axis of the revolving cartridge 100. In another example, the semi-permeable membrane base 114 can be substantially perpendicular with respect to the center aperture 104. In another example, the semi-permeable membrane base 114 is at an angle that is not parallel or perpendicular with one or more of the center aperture 104, a center axis, a top surface 116 of the body 102 or a bottom surface 116 of the body 102 (FIG. 2B). In another example, the semi-permeable membrane base 114 can be oriented at an angle from about 10 degrees to about 80 degrees with respect to one or more of the center aperture 104, a center axis, a top surface 116 of the body 102 or a bottom surface 116 of the body 102.

In one embodiment, the semi-permeable membrane bases 114 can be integrated with the body 102, and optionally formed of the same material as the body 102. In another embodiment, the semi-permeable membrane bases 114 can be configured to be removable from the sample wells 110. As such, the semi-permeable membrane bases 114 can be included as one or more cell culture inserts.

The body 102 and/or semi-permeable membranes 114 can be prepared from various materials suitable with biological experiments and/or cell culture. Materials traditionally used in cell culture dishes and trays can be used to prepare the body 102 and/or membranes 114. In some instance it can be beneficial for the material to be sterilized or sterilizable and may have a single use or reusable format. The materials can be opaque, translucent, transparent, or combinations thereof. For example, the body 102 can be opaque and the semi-permeable membranes 114 can be transparent. The body 102 and semi-permeable membranes 114 can be made from the same material or from different materials, and may be integrated together or separable from each other. The materials for use as the body 102 and/or semi-permeable membranes can include various metals (e.g., stainless steel, etc.), plastics (e.g., cell culture plastics, etc.), ceramics (e.g., silicas or aluminas, etc.) or combinations thereof.

Moreover, the other features associated with the body 102, such as the plugs/caps can be made of the same material as the body 102 and may be integrated or separable. When different materials, the plugs/caps can be prepared from flexibly resistant or elastic materials such as rubbers or elastomers. Elastomers are polymers with viscoelasticity, generally with a low Young's modulus and high yield strain. Examples of elastomers can be unsaturated rubbers, polyisoprenes, polybutadienes, neoprenes, styrene-butatidene rubbers, nitrile rubbers, saturated rubbers, polyacrylic rubbers, silicone rubbers, fluoroelastomers, perfluoroelastomers, polyether block amides, ethylene-vinyl acetates, or the like.

In one embodiment, the body 102 and/or semi-permeable membranes 114 can be transparent. Transparency can be advantageous when the contents of the wells 110 are examined by visual or optical techniques, such as UV-Vis spectroscopy. Accordingly, the membrane 114, and optionally the body 102 can be formed from transparent polymer materials, such as but not limited to, polyethylene terephthalates, polystyrenes, polycarbonates, polyolefins, or combinations thereof.

The body 102 can include one or more plug members 130 located on the top surface 116 radially from the center aperture 104 at an equal distance from the center aperture 104 (or a center axis of the center aperture 104). The plug members 130 can be an equal distance from the sample wells, and can be located between adjacent sample wells 110 on the top surface 116 of the body 102. The plug members 130 can be configured to plug and seal a bottom opening 115 of a sample well 110 of a different revolving cartridge 100 that is placed on top of the revolving cartridge 100 having the plug members 130. The plug members 130 can include a plug feature 134 that is configured as a recess or a protrusion. When a recess, the plug feature 134 can receive an annular member 132 that can operate as a seal. When a protrusion, the plug feature 134 can be the plug 130. In one embodiment, the plug members 130 can each include an o-ring structure as the annular member 132 on a perimeter of the plug member 130 (FIGS. 1A-1C).

The body 102 can include one or more cap members 140 located on the bottom surface 118 radially from the center aperture 104 at an equal distance from the center aperture 104 (or a center axis of the center aperture 104). The cap members 140 can be an equal distance from the sample wells, and can be located between adjacent sample wells 110 on the bottom surface 118 of the body 102. The cap members 140 can be configured to plug and seal a top opening 115 of a sample well 110 of a different revolving cartridge 100 that is placed on top of the revolving cartridge 100 having the cap members 140. The cap members 140 can include a cap feature 144 that is configured as a recess or a protrusion. When a recess, the cap feature 144 can receive an annular member 142 that can operate as a seal. When a protrusion, the cap feature 144 can be the cap member 140. In one embodiment, the cap members 140 can each include an o-ring structure as the annular member 142 on a perimeter of the cap member 140 (FIGS. 1A-1C). The cap members 140 on the bottom surface 118 can be aligned with the plug members 130 on the top surface 116.

The revolving cartridge 100 can include a body 102 having a diameter of about 100 mm to about 200 mm, from about 125 mm to about 175 mm, or from about 140 mm to about 160 mm, or about 150 mm or 160 mm. The body 102 can have a height of about 10 mm to about 100 mm, from about 20 mm to about 90 mm, from about 20 mm to about 75 mm, from about 30 mm to about 70 mm, from about 40 mm to about 60 mm, or about 50 mm. The body 102 can have sample wells 110 with a diameter of about 5 mm to about 50 mm, from about 10 mm to about 30 mm, from about 15 mm to about 25 mm, or about 18 mm or 20 mm.

For example, the wells 110 can be dimensioned as standard cell culture wells, such as the wells in a petri dish of various dimensions, single well plates of various dimensions, 6 well plates (cell growth area of 9.5 cm$^2$ and well diameter of 34.8 mm and a volume of 3 ml to 5 ml per well), 12 well plates (cell growth area of 3.8 cm$^2$ and well diameter of 22.1 mm and a volume of 0.7 mm to 1.8 mm per well), 24 well plates (15.6 diameter wells), and 96 well plates (cell growth area of 0.32 cm$^2$ and diameter of 6.4 mm and well volume of 0.3 ml) or other sizes. The recesses and protrusions can be sized according to the well sizes. The diameter or area of the recesses and protrusions can be substantially the same as the corresponding well diameter or area. The height or a protrusion or depth of a recess can be determined relative to the size of the wells. These heights and depths can be adjusted for the size of the well, where a well that is dimensioned to have a grow area of 0.32 cm$^2$ and diameter of 6.4 mm and well volume of 0.3 ml with a well depth of 12.19 mm can have a corresponding recess or protrusion height of about 0.5 mm, or about 1 mm, or about 2 mm, or any appropriate dimension.

Figure 2C:
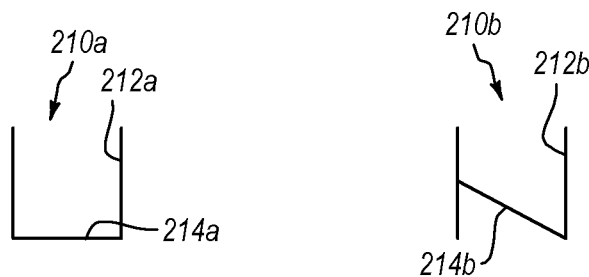
FIGS. 2C-2E include schematic representations of a cross-sectional profile of a bottom surface of a top revolving cell culture cartridge mating with a top surface of a bottom revolving cell culture cartridge, where the features illustrated can be a cap-well interaction, plug-well interaction, or cap-plug interaction.
Figure 2C:
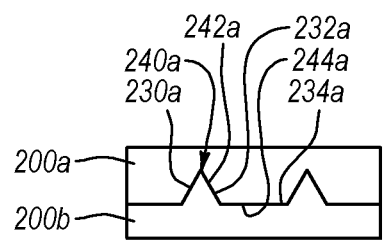
Figure 2D:
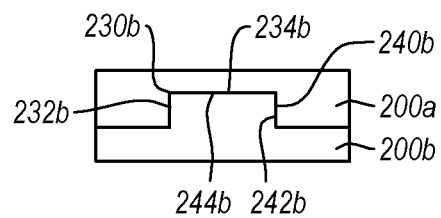
Figure 2E:
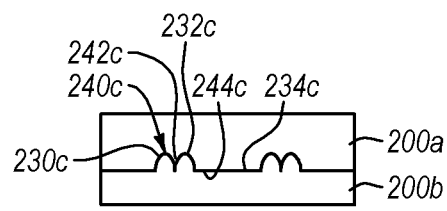
Figure 3A:
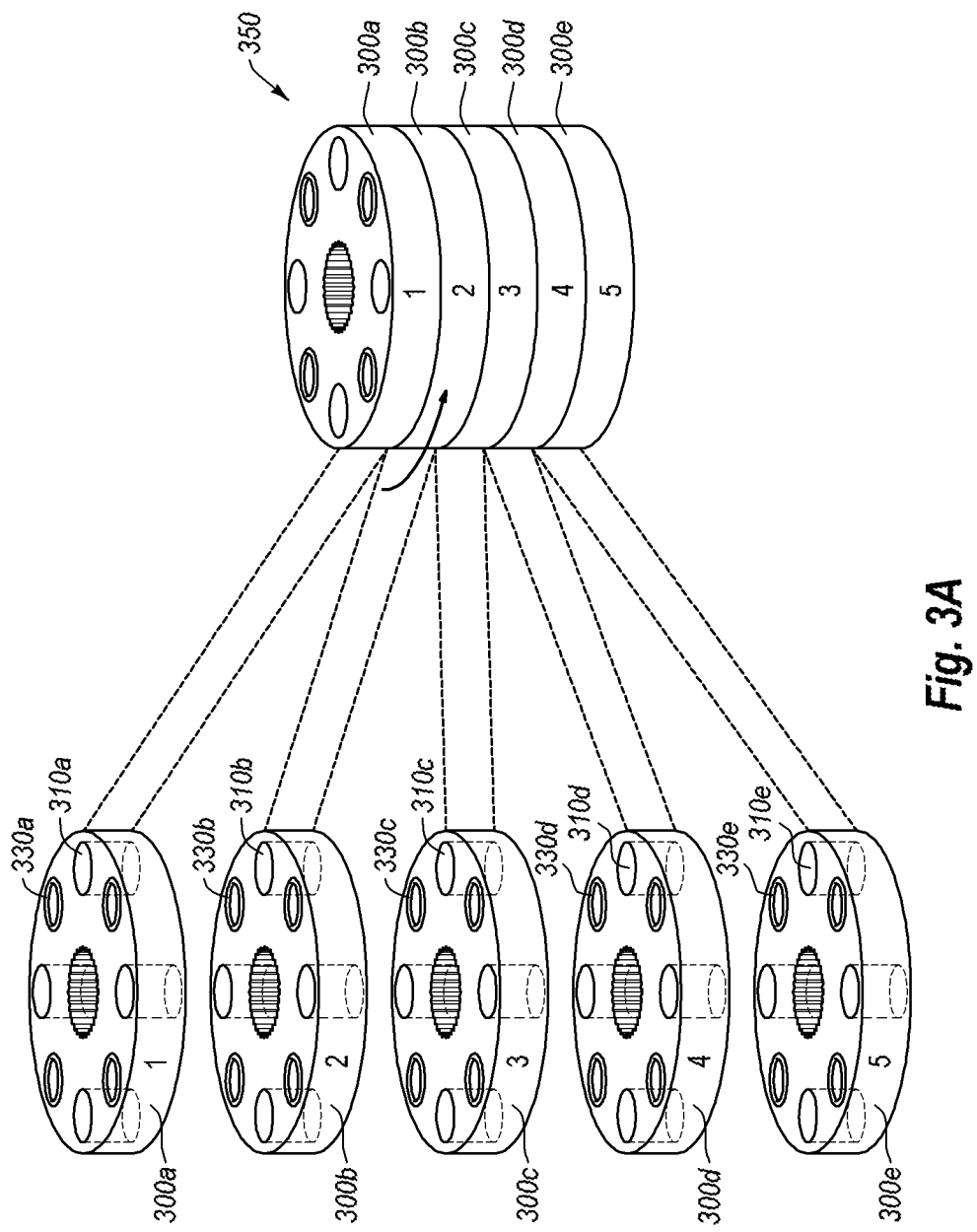

As shown in FIG. 3A, the revolving cartridges 100 are configured to be stacked one on top of the other. As such, the cap members 140 on the bottom surface 118 of a top revolving cartridge 100 serve as caps for the top opening 113 of the sample wells 100 on a bottom revolving cartridge. Also, the plug members 130 on the top surface 116 of a bottom revolving cartridge 100 serve as plugs for the bottom opening 115 of the sample wells 100 of a top revolving cartridge. Accordingly, FIGS. 2C-2E illustrate the plug and cap members of a top revolving cartridge 200a and bottom revolving cartridge 200b. FIG. 2C shows the cap member 240a of a top revolving cartridge 200a mating with the plug member 230a of a bottom revolving cartridge 200b. As shown, the cap member 240a includes an annular protrusion 232a that mates with an annular recess 242a of the plug member 230a, and the cap member 240a includes a recess 244a that mates with a protrusion 234a of the plug member 230a. The protrusion 232a can be an annular ridge-like structure.

FIG. 2D shows the cap member 240b of a top revolving cartridge 200a mating with the plug member 230b of a bottom revolving cartridge 200b. The cap member 240b can be configured as a recess 244b having surfaces 242b that receive and mate with a plug member 230b that is configured as a protrusion 234b having surfaces 232b that receive the surfaces 242b of the cap member 240b. However, the cap member 240b and plug member 230b can be inverted.

FIG. 2E shows the cap member 240c of a top revolving cartridge 200a mating with the plug member 230c of a bottom revolving cartridge 200b. The cap member 240c and plug member 230c can be configured as an interlocking structure. As shown, the plug member 230c includes two annular protrusions 232c with a recess in between that receives a single annular protrusion 242c of the cap member 240c. Also, a plug surface 234c mates with a cap surface 244c.

The plug members and cap members can be configured such that the cap member fits with a top opening of a sample well similar to the fitting with the plug members. Similarly, the plug member can fit with a bottom opening of a sample well similar to fitting with the cap members. For example, with reference to FIGS. 1A-1C, one or more of the plug members 130 and one or more portions of the base surface 118 defining bottom openings 115 of the one or more sample wells 110 are configured to mate and seal such that two revolving cartridges 100 can be stacked and plug the one or more sample wells 110. Optionally, the mating of the one or more plug members 130 with the one or more sample wells 110 is configured as shown in one of FIG. 2C, 2D, or 2E. Also, one or more of the cap members 140 and one or more portions of the top surface 116 defining top openings 113 of the one or more sample wells 110 are configured to mate and seal such that two revolving cartridges 100 can be stacked and cap the one or more sample wells 110. Optionally, the mating of the one or more cap members 140 with the one or more sample wells 110 is configured as shown in one of FIG. 2C, 2D, or 2E.

The plug members and cap members can be formed from the body of the revolving cartridge. Also, the plug members and cap members can have components, such as an o-ring, coupled to or affixed to the body.

Figure 1D:
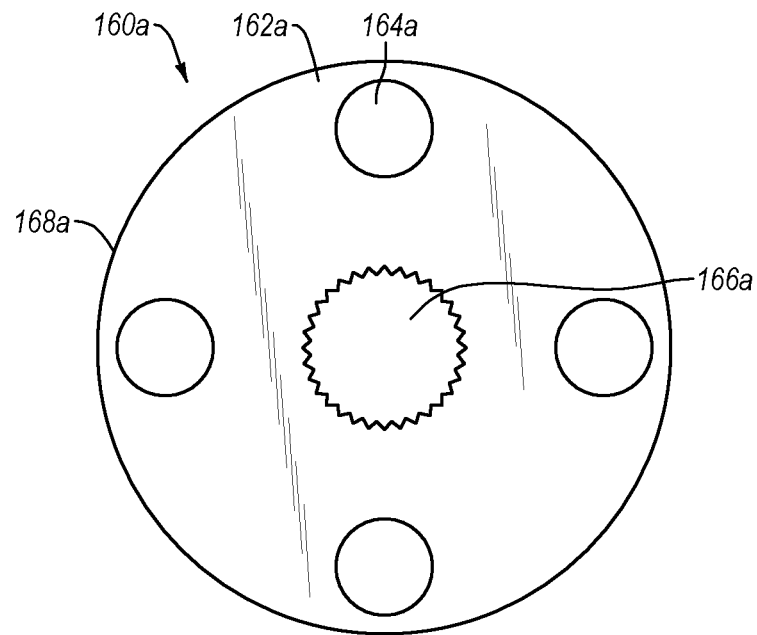
FIGS. 1D-1E include schematic representations of an embodiment of a device for sealing sample wells in a revolving cell culture cartridge.
Figure 1E:
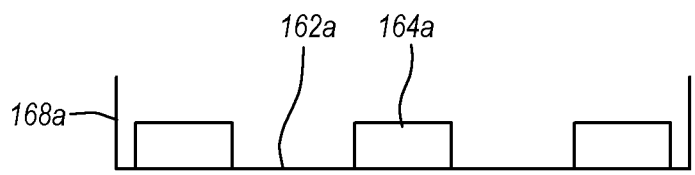

FIGS. 1D-1G illustrate embodiments of seal devices 160a, 160b. The seal devices 160a, 160b are configured features that can be placed within the top opening 113 or bottom opening 115 of a sample well 110 so as to seal the opening. Accordingly, one seal device 160a, 160b can be used to seal the top openings 113 of the revolving cartridge 100 and one seal device 160a, 160b can be sued to seal the bottom openings 115 of the revolving cartridge 100. As shown in FIG. 1D, the seal device 160a can include a body 162a that has two or more seal members 164a. The seal device 160a can include the same number and spacing of seal members 164a as the sample wells 110 of a revolving cartridge 100. Also, the seal device 160a can include a center aperture 166a that corresponds with the center aperture 104 of the revolving cartridge 100. Optionally, FIG. 1E shows that the seal device 160a can include a perimeter wall 168a that can fit against the perimeter surface 117 of the revolving cartridge 100 when coupled thereto.

Figure 1F:
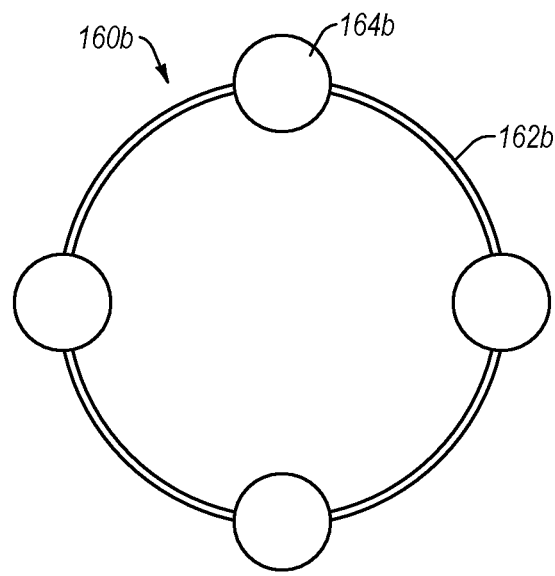
FIGS. 1F-1G include schematic representations of an embodiment of a device for sealing sample wells in a revolving cell culture cartridge.
Figure 1G:
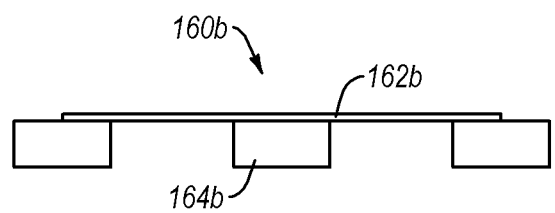

As shown in FIGS. 1F-1G, the seal device 160b can include a ring 162b that has two or more seal members 164b located along the ring 162b. The seal device 160b can include the same number and spacing of seal members 164b as the sample wells 110 of a revolving cartridge 100.

The revolving cartridge 100 can include one or more seal members 164a fit into a top opening 113 or bottom opening 115 of one or more sample wells 110. The revolving cartridge 100 can include one or more seal members 164a located within one or more of the sample wells 110 above and/or below the semi-permeable membrane base 114. The seal members 164a can be located at any distance with relation to the semi-permeable membrane base 114 and the top opening 113 and/or bottom opening 115. There may be gaps between the seal members 164a and the openings 113, 115 and/or membrane 114, or these features can be positioned adjacent and/or touching one another as long as the functionality described herein is retained. For example, the seal members 164a can positioned at the top opening 113 and/or bottom opening 115 of the well 110. In one example, the one or more seal members 164 can be located below the semi-permeable membrane base 114 of one or more of the sample wells 110 and at a bottom surface 118 of the body 102. In another example, a seal member 164a can be located above the semi-permeable membrane base 114 of the one or more sample wells 110 and at a top surface 116 of the body 102.

As shown in FIGS. 3A-3C, two or more of the revolving cartridges 300a-e can be combined into a cartridge stack 350. As shown, revolving cartridges 300a-3 includes sample wells 310a-e and plug members 330a-3, and include cap members which are not shown for clarity. It is understood that the cap members can cap a top opening of a sample well in the same manner as a plug member can plug a bottom opening of a sample well, and disclosure of plug features are considered to also be disclosure of cap features. When in the stack 350, the individual revolving cartridges 300a-e can rotate independent of each other. Such rotation allows for the wells 310b of one revolving cartridge 300b to be aligned with the plug members 330c of a lower revolving cartridge 300c and the cap members (not shown) of an upper revolving cartridge 300a. Such rotation allows for the wells 310b of one revolving cartridge 300b to be aligned with the wells 310c of a lower revolving cartridge 300c and the wells 310a of an upper revolving cartridge 300a.

As shown in FIG. 3B, the top revolving cartridge 300a and bottom revolving cartridge 300b are offset such that the wells 310b on the bottom revolving cartridge 300b are aligned with the plug members 330a of the top revolving cartridge 300a. Accordingly, the wells 310b of the bottom revolving cartridge 300b are aligned with the caps (not shown) on the bottom surface of the top revolving cartridge 300b.

As shown in FIG. 3C, the top revolving cartridge 300a and bottom revolving cartridge 300b are aligned such that the wells 310a of the top revolving cartridge 300a are aligned with the wells 310b of the bottom revolving cartridge 300b. Such an alignment forms a conduit 311 from the top wells 310a and the bottom wells 310b. This can allow for fluid in a top well 310a to pass through the semi-permeable membrane base 314a and into the bottom well 310b. If no plug member plugs the bottom well 310b, the fluid can also pass through the semi-permeable membrane base 314b.

In one embodiment with reference to FIGS. 1A-1C and FIG. 3A-3C, one or more top openings 113 and one or more bottom openings 115 of the one or more sample wells 110 can be configured to mate and seal such that two revolving cartridges 200a-b can be stacked so as to form a fluid conduit 311 between two fluidly coupled sample wells 310a-b of the two revolving cartridges 300a-b.

In one embodiment, the revolving cartridges 300a-b can each include a top surface 116 and bottom surface 118 with one or more stacking features configured to receive another revolving cartridge 300c having the one or more stacking features on its top surface 116 and/or bottom surface 118. The stacking features can include the cap member 140 and plug member 130 as well as the corresponding features associated with the top opening 113 and bottom openings 115 as described herein.

Figure 4A:
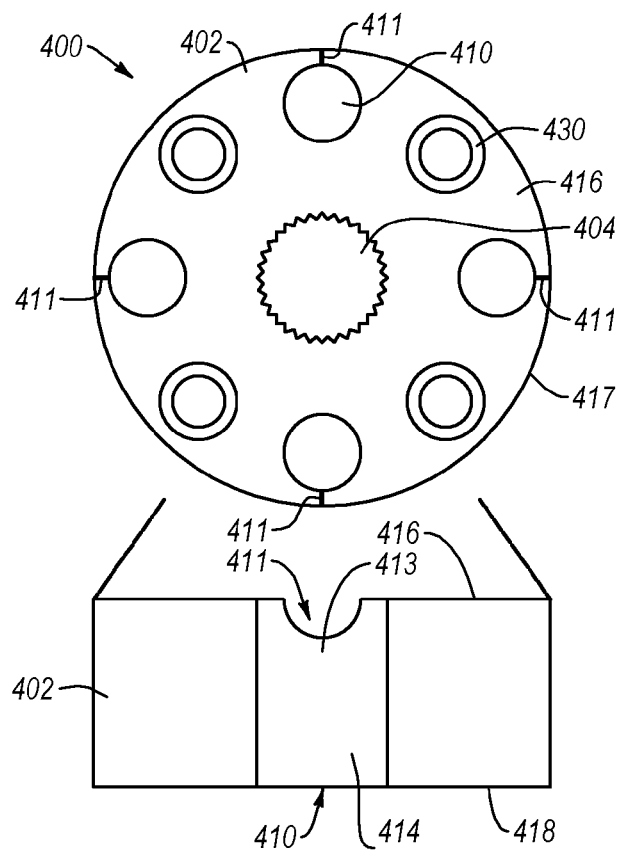
FIGS. 4A-4B include schematic representations of an embodiment of a revolving cell culture cartridge that includes a fluid pathway from a sample well to a perimeter surface of the cartridge.
Figure 4B:
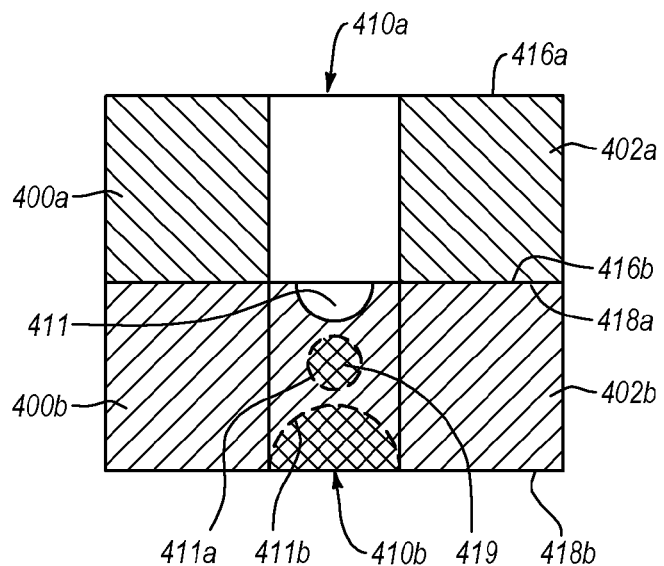

FIGS. 4A-4B show a revolving cartridge 400 that includes a fluid pathway 411 formed into the body 102 in fluid communication with a sample well 410 that allows for fluid to drain or be otherwise removed from the sample well 410. The fluid pathway 411 can include a semi-permeable membrane 419 that can selectively allow some materials to pass therethrough while inhibiting other materials. The semi-permeable membrane 419 can be configured as a semi-permeable membrane 114 described herein, and can be selective to allow gases and/or liquids to pass therethrough. The semi-permeable membrane 419 can also selectively allow test substances and metabolites thereof to pass therethrough while inhibiting the biological substance. The fluid pathway 411 can also include a seal or plug (not shown) that can inhibit any substance from flowing therethrough. The fluid pathway can be dimensioned to have a cross-sectional dimension, such as a diameter for a round fluid pathway, that is significantly less than the dimension of the well. Such dimensions of the fluid pathway can be from about 1% to about 20% of the dimension of the well, from about 2% to about 15%, from about 5% to about 10%, or about 8% of the dimension of the well. The length of the fluid pathway can be adjusted relative to the thickness of the revolving cartridge and the distance from a well to an outer perimeter surface of the revolving cartridge.

Accordingly, the body 402 can have one or more surfaces that define the fluid pathway 411 extending from one or more of the sample wells 414 to a peripheral surface 417 of the body 402. As shown in FIG. 4B, the fluid pathway 411 can be located at the top surface 416. Alternatively, a fluid pathway 411a (e.g., shown by dashed lines) can be located between the top surface 416 and the bottom surface 418. In another alternative, the fluid pathway 411b (e.g., as shown by dashed lines) can be located at the bottom surface 418.

Also shown by FIG. 4B is a top revolving cartridge 400a having a top body 402a that includes a top sample well 410a extending from a top surface 416a to a bottom surface 418a. Also shown is a bottom revolving cartridge 400b having a bottom body 402b that includes a bottom sample well 410b extending from a top surface 416b to a bottom surface 418b. The top sample well 410a is in fluid communication with the bottom sample well 410b so as to form a conduit with the bottom surface 418a of the top revolving cartridge 400a interfacing with the top surface 416a of the bottom revolving cartridge 400b. The bottom revolving cartridge 400b is considered in this example to be an absolute bottom cartridge on the bottom of a stack. The fluid pathway 411, 411a, or 411b allows for pressure to be relieved so that fluid will flow from the top sample well 410a into the bottom sample well 410b.

In some instances, pressure may be needed to move the fluid from a top well to a bottom well in a stack. In such instances, the use of the fluid pathway from a well to the perimeter surface can provide the necessary pressure relief for the fluid to move. If there is no fluid pathway from the well to the perimeter surface, even if pressure is added to the wells on the upper cassette, the liquid cannot follow into the lower well because of the air pressure in the lower well. The fluid pathway allows the air to vent so that pressure allows the fluid to flow down conduits formed from the aligned wells. If there is fluid pathway, the liquid can be pushed into the lower well easily because the air can be pushed outside the well through the fluid pathway.

In some instance, the biological substance can include cells that may need some air to keep the media properly aerated, and the fluid pathway 411 can allow for air to flow therethrough, and may include the semi-permeable membrane 419 to regulate flow. The fluid pathway 411 can be couplable to an gas source (not shown) so that air (e.g., sometimes with sterile regular air, sometimes with air of other compositions) or other gases can flow into and out from the well 410. In one option, the fluid pathway 411 can be configured as a vent to allow for gas within the well 410 to escape.

In one embodiment, the fluid pathway 411 and/or semi-permeable membrane 419 can be configured to control the amount of certain gaseous substances within the well 410. In one example, the semi-permeable membrane 419 can be configured to allow for controlling the amount or flow of substances such as carbon dioxide therethrough.

Figure 5C:
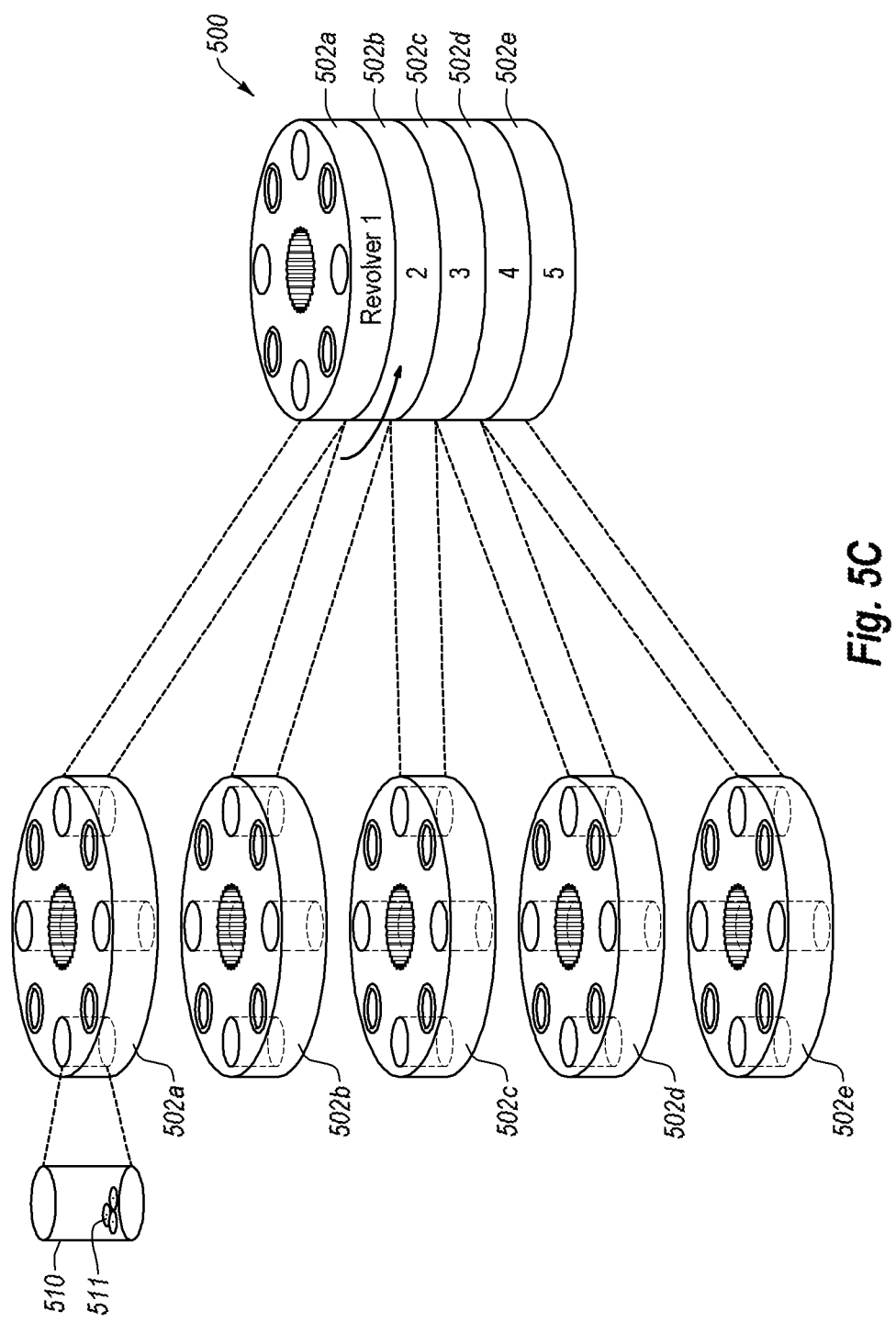

FIGS. 5A-5C illustrate a biological assay system 521 that includes a mechanical spindle 532 and a stack 500 of revolving cartridges 502a-e. The individual revolving cartridges 502a-e can include features described herein, such as sample wells 510 and plug members 530. As shown in FIG. 5A, the spindle 523 can be formed of two or more segments 525a-g and a base 524. Each of the two or more segments 525a-g are mechanically coupled to a revolving actuator 529, which is in turn mechanically coupled to a mechanical system 527. The mechanical system 527 can actuate each of the revolving actuators 529 independently so that the revolving cartridges 502a-e rotate independently. Also, the mechanical system 527 can actuate two or more or all of the revolving actuators 529 at the same time so that two or more or all of the revolving cartridges 502*a-e* rotate at the same time. The mechanical system 527 can be operably coupled to a controller 531 that is configured to control the operation of the mechanical system 527 and control which one or more of the revolving actuators 529 is actuated so as to rotate the revolving cartridges 502*a-e*. The controller 531 can be operably coupled to a computing system 533 that can allow for a user to interface with the computing system 533 so as to implement instructions for the controller 531 to operate the mechanical system 527 and the independent revolving actuators 529. The computing system 533 can include a memory storage medium 535 which can store computer executable instructions for the processing that are then provided to the controller for implementing the instructions with the mechanical system 527 and revolving actuators 529. The computer executable instructions can be in the form of software which can be prepared to perform the assays and methods of operation of the biological assay system 521 as described herein.

In one embodiment, the memory storage medium 535 includes computer executable instructions for rotating the one or more revolving cartridges 502*a-e* independently or together. The memory storage medium 535 can include computer executable instructions for controlling the independent rotational parameters and relative positioning of the one or more revolving cartridges 502*a-e* with respect to each other on the spindle 521 by controlling one or more segments 525 on the spindle 521.

In one embodiment, a biological assay system can include two or more of the revolving cartridges having the features as described herein. The revolving cartridges can be arranged in a stack with their center apertures aligned. The stack of revolving cartridges can be arranged on a spindle or shaft. A spindle can be configured to rotate the individual revolving cartridges by having a spindle surface that applies a force to a surface of the revolving cartridge. On the other hand, a shaft can be smooth such that the revolving cartridges can rotate freely, and can be selectively rotated by an external force, such as by mechanical or by hand.

The spindle can be segmented, where each segment is adapted to be received through the center aperture of a revolving cartridge. Each segment of the spindle can be configured to rotate independently of each other. Optionally, the rotation can be achieved by each segment of the spindle being operably coupled to a mechanical system. The mechanical system can include two or more mechanical components that are rotatably coupled to the two or more segments such that when one of the mechanical components is in operation one of the segments rotates.

In one embodiment, the stacked revolving cartridges can be arranged so that at least two or more revolving cartridges are aligned well to well. Alternatively, the stack can be arranged so that two or more revolving cartridges are not aligned well to well; the revolving cartridges can be aligned well to plug member and/or well to cap member.

In one embodiment, one or more of the revolving cartridges can include a body having a fluid pathway that extends from one or more of the sample wells to a peripheral surface of the body. The stack or revolving cartridges can be arranged so that only the bottom revolving cartridge includes a fluid pathway that extends from one or more of the sample wells to a peripheral surface of the body.

FIG. 5C shows a stack 500 of revolving cartridges 502*a-e* where the sample wells 510 have biological substances 511. The stack 500 of revolving cartridges 502*a-e* can be arranged for a particular distribution of the biological substances 511. For example, the biological substances can be arranged as cells in an intercellular biological pathway. Alternatively, the biological substances can be subcellular components arranged in an intracellular biological pathway. The stack 500 can be used in an assay by proving a liquid medium having a test substance and/or a control substance. The stack 500 can be used in various assays to determine the toxicity, therapeutic benefit, or biological activity on one or more biological substances.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The test substance can be included in an appropriate medium for conducting an experiment. The medium can be medium suitable for an assay, cell growth, or generally suitable for facilitating the interaction between the test substance and the biological substance. Biological fluids or cell culture media are examples of appropriate media. The medium can be a liquid medium, and can be located in one or more of the sample wells of the revolving cartridges. The medium can be located in one or more wells of a top revolving cartridge when the stack of revolving cartridges are staggered, and then top revolving cartridge can be rotated with respect to the next lower revolving cartridge such that the sample wells of each revolving cartridge are aligned in one or more conduits so that the medium and/or its contents can flow into the next lower revolving cartridge. The selective rotation of the revolving cartridges can be performed so that the medium passes from the wells in the top cartridge to the bottom cartridge.

In one embodiment, the medium can include one or more test substances and/or one or more control substances. The test substances and/or control substances can be selected on the type of biological assay to be conducted. The type of test substance can also be used in order to determine and select biological substances that may be part of a biological pathway that processes the test substance. For example, if a test substance is potentially toxic, the biological substances can be known substances that are part of a metabolic pathway that may potentially metabolize the toxic substance. Various biological substances of different metabolic pathways can be included in the different wells of the stacked revolving cartridges. The control substances can have a known positive or negative biological activity with respect to the biological pathway of the biological substances. The test substances can be selected for testing a particular processing, such as metabolism by or incorporation into the biological substances.

In one embodiment, the biological substance occurs naturally, such as by production in a cell. Alternatively, the biological substance can be recombinant. Examples of the biological substance include one or more of nucleic acids, DNA, RNA, proteins, polypeptides, cytokines, hormones, organelles, organs, fluids, lipids, or cells or tissues, or extracellular matrices or components thereof or biologically functional components thereof or markers thereof. Accordingly, the membrane base of each well can be configured for growing cells as well as maintaining subcellular components. The biological substance can also include bacteria, fungi, and viruses and their individual components and cells and subcellular components.

In one embodiment, a biological assay can be performed with a stack of revolving cartridges. One or more biological substances can be introduced into one or more sample wells of the revolving cartridges. However, the stack of revolving cartridges can be prepackaged with a select distribution of biological substances. The stack of revolving cartridges may be prepared and stacked before an assay can be conducted. One or more test substances and/or one or more control substances can be introduced to the one or more biological substances and incubated. The biological substances or product or metabolite thereof can be assayed in order to determine a biological activity of the one or more test substances on the one or more biological substances.

In one embodiment, the biological assay can be conducted manually or by using a mechanical system. The mechanical system can be human controlled or it can be controlled by a computing system. The computing system can include one or more memory storage devices with executable code that directs the mechanical system to rotate the revolving cartridges, such as by: aligning the sample wells of each revolving cartridge so as to form a conduit from a top revolving cartridge to a bottom revolving cartridge; offsetting the sample wells of each revolving cartridge such that a top opening of each sample well in a lower revolving cartridge is closed by a bottom surface with or without a cap member of the adjacent, upper revolving cartridge; offsetting the wells of each revolving cartridge such that a bottom opening of each sample well is closed by a top surface with or without a plug member of the adjacent revolving cartridge; offsetting the sample wells of each revolving cartridge such that a top opening of each sample well is closed by a cap member of a bottom surface of the adjacent revolving cartridge; offsetting the wells of each revolving cartridge such that a bottom opening of each sample well is closed by a plug member of a top surface of the adjacent revolving cartridge.

In one embodiment, the biological assay may also include separating the one or more revolving cartridges and assaying biological substances to determine whether the test substance had a biological effect. The biological assay can also include simultaneously assaying the one or more sample wells of the one or more revolving cartridges, where all wells in all revolving cartridges can be assayed simultaneously, or the wells in a single revolving cartridge can be assayed separately. The biological assay can also include sequentially assaying the one or more sample wells of the one or more revolving cartridges.

The biological assay can include the revolving cartridges being loaded onto a spindle of a centrifuge. Accordingly, the center aperture can be shaped to fit onto a spindle of a centrifuge, and centrifuged.

In one embodiment, the biological assay includes assaying nucleic acid function of the one or more biological substances in the one or more sample wells. Accordingly, nucleic acids can be extracted and purified from the one or more biological substances in the one or more sample wells.

In one embodiment, the biological assay can be conducted to determine toxicity of the one or more test substances. A toxicity assay can be performed by obtaining a test solution that has been passed through a conduit formed from two or more sample wells of adjacent revolving cartridges, and testing the test solution for toxicity. Various toxicity assays that are known for the particular biological substances can be used to determine toxicity. Also, toxicity can be studied at the level of the biological substance at a particular well location within the stack. For example, an MTT toxicity assay can be performed with cells within the stack, and the contents of the sample wells can be monitored by visually or colorometrically analyzing the one or more sample wells (110). The toxicity may also be determined by flow cytometry analysis of the contents of the one or more sample wells having the biological substance.

The biological assays may also be conducted with method steps that include placing one or more sealing members on one or more top or bottom openings of one or more sample wells so as to seal the one or more top or bottom openings. Also, the method steps can include closing or sealing each opening of each sample well.

The biological assays can be conducted by culturing one or more cells in the one or more sample wells of a revolving cartridge or a stack. The cells can be suspension cells or they can be cultured on the permeable membrane base in the sample wells. Alternatively, the cells can be initially cultured on a cell culture insert, which is then introduced into the one or more sample wells.

In one example, a biological assay can include: incubating the test substance and/or control substance with the one or more biological substances in one or more sample wells of a top revolving cartridge; rotating the top revolving cartridge and/or lower revolving cartridge so as to form a fluid conduit between one or more sample wells of the top revolving cartridge and one or more sample wells of the lower revolving cartridge; passing one or more test compositions from one or more of the sample wells in a top revolving cartridge into one or more lower sample wells in a lower revolving cartridge; forming one or more test compositions in one or more of the sample wells in the top revolving cartridge from an interaction between one or more test substances with one or more biological substances; forming one or more second test compositions in one or more sample wells in a second revolving cartridge that is immediately lower, adjacent to the top revolving cartridge from an interaction between contents of the one or more test compositions from the top revolving cartridge; and assaying the one or more test compositions in the one or more revolving cartridges.

In one embodiment, the biological assay can include sequentially incubating one or more test substances and/or one or more sample substances in sample wells from a top revolving cartridge to lower sample wells in a bottom revolving cartridge. The sequential movement of the substance from an upper well to a lower well can be achieved by using pressure to move one or more test compositions from one or more sample wells in a higher revolving cartridge to one or more lower sample wells in a lower revolving cartridge. The sequential movement can be achieved by using gravity to move one or more test compositions from one or more sample wells in a higher revolving cartridge to one or more lower sample wells in a lower revolving cartridge.

The biological assay can include drawing a test composition from a sample well through a fluid pathway that extends radially to a perimeter surface of a revolving cartridge at the bottom of a stack. The withdrawal of fluid from the fluid pathway of the bottom stack can result in the liquid being pulled down a conduit of wells.

Such an assay can include one or more types of cells. The cells can be eukaryotic or prokaryotic. The cells can be primary cultures, tissues, immortalized cell lines, and the like. The cells can be from various organisms that include plants, animals, insects, monera, protista, fungi, archaea, chromista, or others. Examples of cell types can include mucous membrane cells of the large intestine, mucous membrane cells of the small intestine, skin cells, mucous membrane cells of the stomach, liver cells, kidney cells, heart muscle cells, blood vessel cells, and any other type of cell. In one example, the biological substance includes a microorganism, and each revolving cartridge in a stack can include one or more types of microorganisms. Examples of microorganisms include *Actinomycetes, Bacillus subtilis*, yeast, *Aspergillus*, and any other type of microorganism.

Examples of cell types can further include prokaryotic cells, eukaryotic cells, bacteria, archaea, epithelium cell, epidermal, epidermal keratinocyte, epidermal basal cell, keratinocytes, basal cell, medullary hair shaft cell, cortical hair shaft cell, cuticular hair shaft cell, cuticular hair root sheath cell, hair matrix cell, wet stratified barrier epithelial cells, gland cells, hormone secreting cells, metabolism cells, storage cells, barrier function cells, ciliated cells, extracellular matrix secretion cells, contractile cells, blood cells, immune system cells, nervous system cells, pigment cells, germ cells, nurse cells, interstitial cells, or others as well as combinations thereof.

In one example, a biological assay can include: step (a) allowing or inducing apoptosis or inflammation reactions to occur in one or more test compositions in one or more sample wells of a higher revolving cartridge; step (b) eluting one or more test compositions from the higher revolving cartridge to one or more sample wells of a lower revolving cartridge; and optionally, repeating steps (a) and (b) into one or more lower revolving cartridges; and assaying contents of the one or more sample wells in the one or more revolving cartridges to determine whether a protein or lower molecular weight biological products are produced, released, modified, or upregulated.

In one embodiment, the biological assay can include determining whether or not the one or more test substances induce, increase, inhibit, reduce or modulate an allergic response. The allergic assay can include: incubating one or more test components in one or more sample wells of a first revolving cartridge with one or more epithelial cells so as to produce one or more first test compositions; eluting the one or more first test compositions of the one or more sample wells in the first revolving to one or more sample wells in a second revolving; incubating the one or more first test compositions with immune system biological substances and/or cells in one or more sample wells of the second revolving; and determining whether or not the one or more test components cause the one or more epithelial cells to produce an immune product.

In one embodiment, the biological assay can include method steps to determine whether or not one or more test compounds caused one or more biological substances in one or more sample wells of the first revolving cartridge to produce a protein or lower molecular weight biological product.

In one embodiment, the biological assay can include filtering a test composition by the permeable membrane base when passing content of a sample well in a higher revolving cartridge to a fluidly coupled sample well in a lower revolving cartridge.

In one embodiment, the biological assay can include method steps to determine whether or not metabolism of one or more test substances occurs by one of the biological substances. The assays can also determine comparatively more effective metabolic pathways of a biological substance, such as a microorganism.

In one embodiment, the biological assay can include obtaining one or more biological substances from one or more organs or tissues, and then placing the biological substances in the sample wells of the revolving cartridges.

In one embodiment, the biological assay can include method steps to determine survival rate of cells in one or more sample wells of one or more revolving cartridges after incubation with one or more test substances and/or one or more control substances.

In one embodiment, the biological assay can include method steps for performing a glutathione quantitative analysis of contents of one or more sample wells of one or more revolving cartridges to determine if test substance inhibits toxicity.

In one embodiment, the biological assay can include method steps for performing gene expression analysis of contents of one or more sample wells of one or more revolving cartridges. In another embodiment, the biological assay can include method steps for determining whether or not gene expression has changed in response to the one or more test substances and/or control substances.

In one embodiment, the biological assay can include method steps for arranging one or more sample wells in one or more revolving cartridges for a detoxification path. A detoxification pathway can be analyzed for detoxification metabolism in one or more sample wells of one or more revolving cartridges. A detoxification pathway can also be analyzed for detoxification metabolism by one or more biological substances in one or more sample wells of one or more revolving cartridges.

In one embodiment, the biological assay can include method steps for performing an environmental toxicity assay in one or more sample wells in one or more revolving cartridges.

In one embodiment, the biological assay can include method steps for assaying interaction of one or more test substances with cells or tissue from one or more of liver, heart, or kidney.

In one embodiment, the biological assay can include method steps for configuring two or more revolving cartridges as one or more of the following: including one or more mucous membrane cells from one or more of large intestine, small intestine, or stomach in one or more sample wells of a first revolving cartridge; including one or more skin cells in one or more sample wells of a first revolving cartridge; including one or more heart muscle cells in one or more sample wells in a second revolving cartridge below the first revolving cartridge; including one or more blood vessel cells in one or more sample wells in a second revolving cartridge below the first revolving cartridge; including one or more kidney cells in one or more sample wells in a second revolving cartridge below the first revolving cartridge; including one or more liver cells in one or more sample wells in a second revolving cartridge below the first revolving cartridge.

In one embodiment, the biological assay can include method steps for configuring two or more revolving cartridges as one or more of the following: including one or more types of microorganisms in one or more sample wells of a first revolving cartridge; including one or more types of microorganisms in one or more sample wells in a second revolving cartridge below the first revolving cartridge, wherein the microorganisms in the first revolving cartridge and second revolving cartridge are the same or different.

In one embodiment, the biological assay can include method steps for identifying a compound or substance produced or upregulated during the assay. This can include identifying a compound or substance produced or upregulated during the assay that inhibits toxicity of one or more test substances and/or control substances.

In one embodiment, the biological assay can include stomach mucous membrane cells, cell monolayer sheet, or tissue. Apoptosis or inflammation reaction is induced in the cells by the test substance and/or control substance. The cell content is eluted, and an agent of the immune reaction in response to the test substances and/or control substance is released. The effect of the agent to the cells in lower revolving cartridge wells can be studied. Part of the upper level revolver can be used to evaluate if a protein or low molecular weight compound is released in response to the test substance or control substance. The protein or low molecular weight compound can be studied to determine if it can cause an allergic reaction to epithelial tissue, like skin, oral mucous membrane or stomach mucous membrane. For example, if a cell cocktail of the immune system is put on the lower revolver, the possibility that there is a possibility of the substance released from the first revolver can cause critical immune reaction can be evaluated.

In one embodiment, a stack of revolving cartridges can be used to study a cytokine induction, and may be used to study or create a cytokine induction model. A method of using the stack of revolving cartridges can include introducing appropriate cells, such as cultured cells, into one or more wells of the revolving cartridges, which can include wells of each of the vertically adjacent wells in vertically adjacent revolving cartridges. The method can include introducing an inducing substance to induce the cultured cells in a top revolving cartridge to produce a cytokine, such as the cytokine IL-6. The inducing agent to produce cytokine IL-6 can be a lipopolysaccharide (LPS), which can be provided in a suitable amount. The inducing substance can be incubated with the cells for an arbitrary time period or predetermined time period. During incubation, the next lower revolving cartridge can be staggered with respect to the top revolving cartridge having the cells and inducing agent such that the next lower revolving cartridge plugs the bottom of each well of the top revolving cartridge. After an arbitrary or predetermined time period, the top revolving cartridge and next lower revolving cartridge can be rotated with respect to each other (e.g., one or the other, or both, are rotated) so as to align vertically adjacent wells in the top revolving cartridge and next lower revolving cartridge so that a conduit is formed between the wells and fluidic content of the wells in the top revolving cartridge can flow into the vertically adjacent and aligned wells of the next lower revolving cartridge. The wells of the next lower revolving cartridge can be the same as the wells of the top revolving cartridge, or they can be different. For examples, the cells in the next lower revolving cartridge can be cells that interact with a cytokine, such as IL-6, in a biological pathway. The contents from the wells in the top revolving cartridge can include the cytokine IL-6 as well as other substances. Together, all of the fluidic substances of the wells of the top revolving cartridge flow through the permeable membrane and into the wells of the next lower revolving cartridge. Some of the contents of the wells of the top revolving cartridge can be withdrawn for analysis. The contents of the wells in the top revolving cartridge including the cytokine can then be incubated with the cells in the wells of the next lower revolving cartridge for an arbitrary or predetermined time period. Such incubation can allow for an interaction between the cytokine IL-6 and the cells sufficient to cause progress through a biological pathway, such as causing the cells to differentiation, undergo apoptosis, or generate other chemical substances. The resulting composition from incubating the cells and cytokine IL-6 can in the wells of the next lower revolving cartridge can then be withdrawn for analysis. The analysis can identify the types and amounts of substances that were generated in the wells of the next lower revolving cartridge as well as changes in types and amounts of substances from the wells of the top revolving cartridge. This process can be repeated into the vertically adjacent wells of the subsequent next lower revolving cartridge, and can continue through all of the revolving cartridges in a stack.

In one embodiment, the inducing substance can be an endotoxin and the cells can be vascular endothelial cells of the brain. It is expected that incubation of the endotoxin and vascular endothelial cells of the brain can stimulate production of prostaglandin E2. The revolving cartridge system can be used to verify whether the incubation matches a disease model.

In one embodiment, a stack of revolving cartridges can be used to study a apoptosis, and may be used to study or create an apoptosis model. A method of using the stack of revolving cartridges can include introducing appropriate cells, such as cultured cells, into one or more wells of the revolving cartridges, which can include wells of each of the vertically adjacent wells in vertically adjacent revolving cartridges. The method can include introducing an apoptosis substance or substances being tested to determine whether it induces apoptosis to the cultured cells in a top revolving cartridge to induce an apoptosis event or produce apoptosis factors. The apoptosis substance can be a tumor necrosis factor (TNF) or Fas ligand that interacts with a Fas receptor (e.g., Apo-1 or CD95) to produce apoptosis factors or apoptosis signaling events. The apoptosis substance can be incubated with the cells for an arbitrary time period or predetermined time period. During incubation, the next lower revolving cartridge can be staggered with respect to the top revolving cartridge having the cells and inducing agent such that the next lower revolving cartridge plugs the bottom of each well of the top revolving cartridge. After an arbitrary or predetermined time period, the top revolving cartridge and next lower revolving cartridge can be rotated with respect to each other (e.g., one or the other, or both, are rotated) so as to align vertically adjacent wells in the top revolving cartridge and next lower revolving cartridge so that a conduit is formed between the wells and fluidic content of the wells in the top revolving cartridge can flow into the vertically adjacent and aligned wells of the next lower revolving cartridge. Optionally, the cells in the wells of the top revolving cartridge, such as apoptotic cells, can be allowed to pass through to the wells of the next lower revolving cartridge. The wells of the next lower revolving cartridge can be the same as the wells of the top revolving cartridge, or they can be different. For examples, the cells in the next lower revolving cartridge can be macrophages. The contents from the wells in the top revolving cartridge can include the apoptosis substance as well as other substances. Together, all of the fluidic substances of the wells of the top revolving cartridge, and optionally cells, flow through the permeable membrane and into the wells of the next lower revolving cartridge. The permeable membrane can be dimensioned to allow or inhibit cells from passing therethrough. This can also include dimensions that inhibit live cells from passing through, but allow for dead cells or apoptotic cells to pass through. Some of the contents of the wells of the top revolving cartridge can be withdrawn for analysis. The contents of the wells in the top revolving cartridge can then be incubated with the cells in the wells of the next lower revolving cartridge for an arbitrary or predetermined time period. Such incubation can allow for an interaction between the apoptotic factors or substances associated with an apoptotic event and the cells sufficient to cause progress through a biological pathway, such as causing the cells to differentiation, undergo apoptosis, or generate other chemical substances. The resulting composition from the incubation in the wells of the next lower revolving cartridge can then be withdrawn for analysis. The analysis can identify the types and amounts of substances that were generated in the wells of the next lower revolving cartridge as well as changes in types and amounts of substances from the wells of the top revolving cartridge. This process can be repeated into the vertically adjacent wells of the subsequent next lower revolving cartridge, and can continue through all of the revolving cartridges in a stack.

In one embodiment, the inducing substance can be an endotoxin and the cells can be vascular endothelial cells of the brain. It is expected that incubation of the endotoxin and vascular endothelial cells of the brain can stimulate production of prostaglandin E2. The revolving cartridge system can be used to verify whether the incubation matches a disease model.

In one embodiment, the agent introduced into the wells of the top revolving cartridge can be an apoptotic agent that induces apoptosis. The apoptotic agent can be a natural agent, such as an extracellular factor. An example of such an apoptotic agent can include the Fas ligand. The Fas ligand can interact with a Fas receptor such that the apoptosis cell (e.g., cell in well of top revolving cartridge) can release ATP and UTP. The ATP and UTP can interact with a macrophage, such as P2Y2, which has an ATP/UTP receptor. The macrophage can be in the wells of the next lower revolving cartridge. Therefore, the apoptotic agent can be tested to determine if it induces apoptosis in the cell, and the cellular contents or apoptotic cell can then be introduced into the wells of the next lower revolving cartridge. The interaction of the contents of the wells in the top revolving cartridge with the cells in the wells of the next lower revolving cartridge can be observed and analyzed.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In an illustrative embodiment, any of the operations, processes, etc. described herein can be implemented as computer-readable instructions stored on a computer-readable medium. The computer-readable instructions can be executed by a processor of a mobile unit, a network element, and/or any other computing device.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

The invention claimed is:

1. A cell device comprising:
a revolving cartridge having a unitary body defining:
   a center aperture; and
   two or more evenly spaced sample wells that are spaced apart from each adjacent sample well by at least the diameter of each sample well, each sample well positioned radially equidistant from the center aperture, wherein each sample well has a top opening formed into the top surface of the unitary body and a bottom opening formed in the bottom surface of the unitary body; and
a semi-permeable membrane base in each sample well that is configured to fluidly couple the top surface and the bottom surface of the unitary body.

2. The cell device of claim 1, wherein the center aperture is defined by one or more walls having a shape configured to receive a shaft therethrough such that the revolving cartridge is fixed with respect to the shaft so that rotation of the shaft rotates the revolving cartridge and when the shaft is static the revolving cartridge is static.

3. The cell device of claim 1, wherein the semi-permeable membrane base is oriented at an angle from about 10 degrees to about 80 degrees with respect to one or more of the center aperture, a center axis, a top surface of the body or a bottom surface of the body.

4. The cell device of claim 1, further comprising one or more plug members located radially from the center aperture at an equal distance from a center axis with each sample well and located between adjacent sample wells on the top surface and/or the bottom surface of the body, wherein the one or more plug members include structure selected from the group consisting of an o ring structure, a ridge structure, a cap structure, and an interlock structure.

5. The cell device of claim 4, wherein one or more of the plug members and one or more portions of the base surface defining bottom openings of the one or more sample wells are configured to mate and seal such that two revolving cartridges can be stacked and plug the one or more sample wells when sample wells of the two revolving cartridges are offset, and wherein one or more the top openings and one or more of the bottom openings of the one or more sample wells are configured to make and seal such that two revolving cartridges are capable of being stacked so as to form a fluid conduit between two fluidly coupled sample wells of the two revolving cartridges when sample wells of the two revolving cartridges are aligned.

6. A cell device system comprising:
two or more revolving cartridges each having a body including a center aperture and two of more evenly spaced sample wells that are spaced apart from each adjacent sample well by at least the diameter of each sample well, each sample well positioned radially equidistant from the center aperture, wherein each sample well has a semi-permeable membrane base configured to fluidly couple a top surface and a bottom surface of the body, and wherein each sample well has a top opening formed into the top surface of the body and a bottom opening formed in the bottom surface of the body, wherein the two or more revolving cartridges are stacked with their center apertures aligned.

7. The cell device system of claim 6, wherein the two or more revolving cartridges are stacked on a spindle, wherein the spindle is segmented, each segment adapted to be received through the center aperture of one of the revolving cartridges; and wherein the each segment of the spindle is configured to rotate independently of each other so as to independently rotate the revolving cartridges.

8. The cell device system of claim 7, wherein each segment of the spindle is operably coupled to a mechanical system, wherein the mechanical system includes two or more mechanical components rotatably coupled to the two or more segments such that when one of the mechanical components operate one of the segments rotate.

9. The cell device system of claim 8, wherein the mechanical system is operably coupled to a controller, wherein the controller is operably coupled to a computing system including a memory storage medium, wherein the memory storage medium includes computer executable instructions selected from the group consisting of:
computer executable instructions for performing one or more assays;
computer executable instructions for rotating one or more of the revolving cartridges independently or together; and
computer executable instructions for controlling independent rotational parameters and relative positioning of the revolving cartridges with respect to each other on the spindle by controlling one or more segments on the spindle.

10. An assay method comprising:
providing one or more of the cell device systems of claim 6;
introducing one or more biological substances into one or more sample wells of the two one or more revolving cartridges;
introducing one or more test substances and/or one or more control substances to the one or more biological substances; and
assaying the biological substances to determine a biological activity of the one or more test substances on the one or more biological substances.

11. The method of claim 10, further comprising: one or more of the following:
stacking two or more of the revolving cartridges with their center apertures aligned;
aligning the sample wells of two or more stacked revolving cartridge so as to form a conduit from a top revolving cartridge to a bottom revolving cartridge;
offsetting the sample wells of adjacent revolving cartridges such that a top opening of each sample well of a bottom revolving cartridge is closed by the bottom surface of the adjacent revolving cartridge above the bottom revolving cartridge;
offsetting the sample wells of each revolving cartridge such that a bottom opening of each sample well in a top revolving cartridge is closed by top surface of the adjacent revolving cartridge below the top revolving cartridge;
offsetting the sample wells of each revolving cartridge such that the top opening of each sample well of a bottom revolving cartridge is closed by a plug member of the bottom surface of the adjacent revolving cartridge above the bottom revolving cartridge;
offsetting the wells of each revolving cartridge such that the bottom opening of each sample well in a top revolving cartridge is closed by a plug member of the top surface of the adjacent revolving cartridge below the top revolving cartridge; or
separating two or more revolving cartridges.

12. The method of claim 10, further comprising one or more of the following:
simultaneously assaying the one or more sample wells of the one or more revolving cartridges;
sequentially assaying the one or more sample wells of the one or more revolving cartridges;
assaying the one or more sample wells of the one or more revolving cartridges separately from each other; or
centrifuging the one or more revolving cartridges.

13. The method of claim 10, further comprising one or more of the following:
assaying nucleic acid function of the one or more biological substances in the one or more sample wells;
extracting or purifying a nucleic acid from the one or more biological substances in the one or more sample wells; or
determining toxicity of the one or more test substances.

14. The method of claim 10, further comprising one or more of the following:
closing or sealing each opening of each sample well;
culturing the one or more cells in the one or more sample wells;
culturing one or more cells on a semi-permeable membrane base on the cell culture insert and introducing the cell culture insert into the one or more sample wells;
introducing the test substance and/or control substance into one or more of the sample wells of a top revolving cartridge; or
incubating the test substance and/or control substance with the one or more biological substances in one or more sample wells of a top revolving cartridge.

15. The method of claim 10, further comprising one or more of the following:

rotating a top revolving cartridge and/or lower revolving cartridge so as to form a fluid conduit between one or more sample wells of the top revolving cartridge and one or more sample wells of the lower revolving cartridge;

passing one or more test compositions from one or more of the sample wells in a top revolving cartridge into one or more lower sample wells in a lower revolving cartridge;

forming one or more test compositions in one or more of the sample wells in a top revolving cartridge from an interaction between one or more test substances with one or more biological substances;

forming one or more second test compositions in one or more sample wells in a second revolving cartridge that is immediately lower, adjacent to the top revolving cartridge from an interaction between contents of the one or more test compositions from the top revolving cartridge;

assaying the one or more test compositions in the one or more revolving cartridges;

sequentially incubating one or more test substances and/or one or more sample substances in sample wells from a top revolving cartridge to lower sample wells in a bottom revolving cartridge.

16. The method of claim 10, further comprising one or more of the following:

using pressure to move one or more test compositions from one or more sample wells in a higher revolving cartridge to one or more lower sample wells in a lower revolving cartridge;

using gravity to move one or more test compositions from one or more sample wells in a higher revolving cartridge to one or more lower sample wells in a lower revolving cartridge; or drawing a test composition from a sample well through a fluid pathway that extends radially to a perimeter surface of a revolving cartridge.

17. The method of claim 10, further comprising:

step (a) allowing or inducing apoptosis or inflammation reactions to occur in one or more test compositions in one or more sample wells of a higher revolving cartridge;

step (b) eluting one or more test compositions from the higher revolving cartridge to one or more sample wells of a lower revolving cartridge; and optionally, repeating steps (a) and (b) into one or more lower revolving cartridges.

18. The method claim 10, further comprising:

incubating one or more test substances in the one or more sample wells of a first revolving cartridge with one or more epithelial cells so as to produce one or more first test compositions;

eluting the one or more first test compositions of the one or more sample wells in the first revolving cartridge to the one or more sample wells in a second revolving cartridge;

incubating the one or more first test compositions with immune system biological substances and/or cells in the one or more sample wells of the second revolving cartridge;

determining whether or not the one or more test substances cause the one or more epithelial cells to produce an immune product.

19. The method of claim 18, further comprising determine whether or not the one or more test substances cause the one or more biological substances in the one or more sample wells of the first revolving cartridge to produce a protein or lower molecular weight biological product.

20. The method of claim 10, further comprising configuring two or more revolving cartridges as one or more of the following:

including one or more mucous membrane cells from one or more of large intestine, small intestine, or stomach in one or more sample wells of a first revolving cartridge;

including one or more skin cells in one or more sample wells of a first revolving cartridge;

including one or more heart muscle cells in one or more sample wells in a second revolving cartridge below the first revolving cartridge;

including one or more blood vessel cells in one or more sample wells in a second revolving cartridge below the first revolving cartridge;

including one or more kidney cells in one or more sample wells in a second revolving cartridge below the first revolving cartridge;

including one or more liver cells in one or more sample wells in a second revolving cartridge below the first revolving cartridge.

* * * * *